United States Patent [19]
Lubisch et al.

[11] Patent Number: 4,959,373
[45] Date of Patent: Sep. 25, 1990

[54] BISPIDINE DERIVATIVES AS CLASS III ANTIARRHYTHMIC AGENTS

[75] Inventors: Wilfried Lubisch, Mannheim; Fritz Binnig, Fussgoenheim; Gerda von Philipsborn, Weinheim, all of Fed. Rep. of Germany

[73] Assignee: BASF Aktiengesellschaft, Ludwigshafen, Fed. Rep. of Germany

[21] Appl. No.: 247,645

[22] Filed: Sep. 22, 1988

[30] Foreign Application Priority Data

Sep. 24, 1987 [DE] Fed. Rep. of Germany ....... 3732094

[51] Int. Cl.$^5$ ........................................... C07D 471/02
[52] U.S. Cl. ..................................... 514/300; 546/122
[58] Field of Search ......................... 514/300; 541/122

[56]  References Cited
U.S. PATENT DOCUMENTS 4,459,301  7/1984  Binnig et al. .................. 546/122

FOREIGN PATENT DOCUMENTS 62199   10/1982  European Pat. Off. .
158775  10/1985  European Pat. Off. .
164165  12/1985  European Pat. Off. .
178874   4/1986  European Pat. Off. .
2726571 12/1978  Fed. Rep. of Germany .

OTHER PUBLICATIONS

Ruenitz et al., Antiarrhythmic Activity of Some N-Alkylbispidinebenzamides, 1979, vol. 22, No. 9, J. M. Chem.
Galvez et al., Struct. and Conform. Study of Diazabicyclanones & Diazabicyclanols, J. Mol. Struct., 1985, 127(3-4).
Gubasheva et al., deposited doc., 1982, 3359-82, 12 pp. Synthesis and Stereochemistry of Heteroanalogs. . .

*Primary Examiner*—Mary C. Lee
*Assistant Examiner*—Catherine Scalzo
*Attorney, Agent, or Firm*—Oblon, Spivak, McClelland, Maier & Neustadt

[57]  ABSTRACT

Bispidine derivatives of the formula I

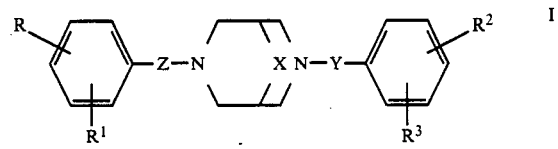

where R, $R^1$ and $R^3$ are identical or different and are each H, $C_1$–$C_4$-alkyl, halogen or $C_1$–$C_4$-alkoxy, when Y is

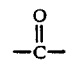

$R^2$ is $C_1$–$C_4$-alkyl, halogen, —CN, $C_1$–$C_4$-alkoxy, —NHSO$_2$CH$_3$, —CF$_3$, NH-acetyl or —NR$^4$R$^5$ where $R^4$ and $R^5$ are each $C_1$–$C_4$-alkyl, when Y is

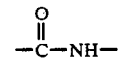

$R^2$ is $C_1$–$C_4$-alkyl, halogen, —CN$_1$$C_1$–$C_4$-alkoxy, —NHSO$_2$CH$_3$, —CF$_3$, NH-acetyl or —NR$^9$R$^{10}$ where $R^9$ is $C_1$–$C_4$-alkyl and $R^{10}$ is H or $C_1$–$C_4$-alkyl, and when X is not CH$_2$ R$_2$ may also be NO$_2$ or NH$_2$, X is —CH$_2$—, —C(O)— or —C(R$^6$)OR$^7$— (where R$^6$ is H or $C_1$–$C_4$-alkyl and $R^7$ is H, $C_1$–$C_4$-alkyl or

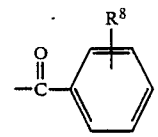

where $R^8$ is H, $C_1$–$C_4$-alkyl, halogen or $C_1$–$C_4$-alkoxy), Y is —C(O) or —CONH— and Z is $C_1$–$C_4$-alkylene which may be olefinically unsaturated and/or branched, and their physiologically tolerated salts, and drugs containing these compounds as active compounds are described.

11 Claims, No Drawings

BISPIDINE DERIVATIVES AS CLASS III ANTIARRHYTHMIC AGENTS

The present invention relates to novel bispidine derivatives, drugs containing these derivatives and their use for the preparation of antiarrhythmic agents of Class III according to Vaughan-Williams.

The antiarrhythmic agents can be classified in 4 groups according to Vaughan-Williams: I. sodium antagonists, II. adrenergic β-receptor blockers, III. potassium channel inhibitors and IV. calcium antagonists.

Bispidine derivatives are known to be antiarrhythmic agents (Peter C. Ruenitz and Corwin M. Mokler, J. Med. Chem. 22 (1979), 1142, EP-A-62 199 and DE-A-27 26 571). Because of their action mechanism, they are for the most part sodium antagonists belonging to Class I according to Vaughan-Williams.

Class III antiarrhythmic agents are often preferred in therapy since they are effective in arrhythmias which are otherwise resistant to therapy. Class III antiarrhythmic agents lead to an extension of the QT interval in the ECG without affecting the PQ interval and without pronounced reduction of the heart rate.

Such agents are disclosed, for example, in EP-A-164 165, EP-A-178 874 and EP-A-158 775.

We have found that bispidine derivatives of the formula I

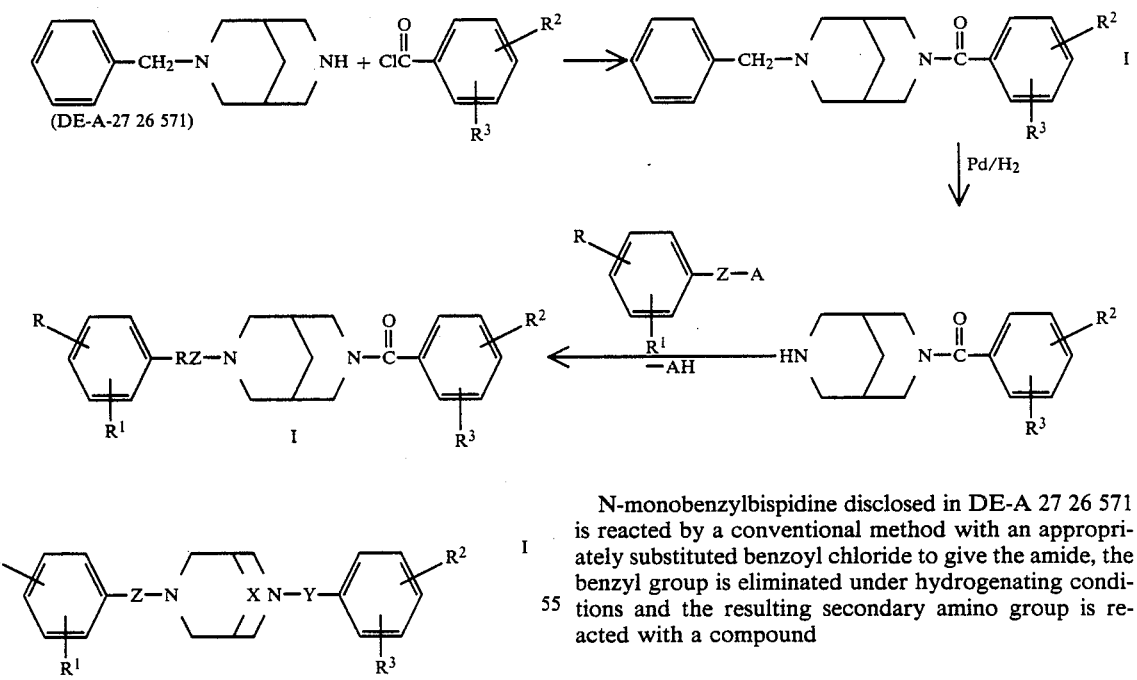

where R, $R^1$ and $R^3$ are identical or different and are each H, $C_1$-$C_4$-alkyl, halogen or $C_1$-$C_4$-alkoxy, $R^2$ is $$Y = -\overset{O}{\underset{\|}{C}}-$$

$C_1$-$C_4$-alkyl, halogen, —CN, $C_1$-$C_4$-alkoxy, —NHSO$_2$CH$_3$, —CF$_3$, NH-acetyl or —NR$^4$R$^5$ where R$^4$ and R$^5$ are each $C_1$-$C_4$-alkyl, when Y is

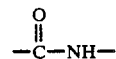

$R^2$ is $C_1$-$C_4$-alkyl, halogen, —CN, $C_1$-$C_4$-alkoxy, —NHSO$_2$CH$_3$, —CF$_3$, NH-acetyl or NR$^9$R$^{10}$ where R$^9$ is $C_1$-$C_4$-alkyl and R$^{10}$ is H or $C_1$-$C_4$-alkyl, and when X is not CH$_2$ R$^2$ may also be NO$_2$ or NH$_2$, —CH$_2$—, —C(O)— or —C(R$^6$)OR$^7$— (where R$^6$ is H or $C_1$-$C_4$-alkyl and R$^7$ is H, $C_1$-$C_4$-alkyl or

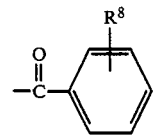

where R$^8$ is H, $C_1$-$C_4$-alkyl, halogen or $C_1$-$C_4$-alkoxy), Y is —C(O) or —CONH— and Z is $C_1$-$C_4$-alkylene which may be olefinically unsaturated and/or branched, and their physiologically tolerated salts have superior properties.

$R^3$ is preferably hydrogen, X is preferably —CH$_2$— or —CO—, Y is preferably —CONH— and Z is preferably methylene.

The novel compounds can be prepared, for example, according to the following equations A to C: Equation A:

N-monobenzylbispidine disclosed in DE-A 27 26 571 is reacted by a conventional method with an appropriately substituted benzoyl chloride to give the amide, the benzyl group is eliminated under hydrogenating conditions and the resulting secondary amino group is reacted with a compound

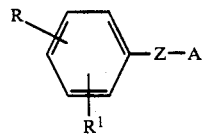

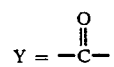

where R, $R^1$ and Z have the above meanings and A is a leaving group, to give the end product I. Leaving group A, which can be displaced by nucleophiles, may be, for example, chlorine, bromine, methoxy, ethoxy, an oxysuccinimide radical, 1-imidazolyl or ethoxycarbonyloxy. Equation B:

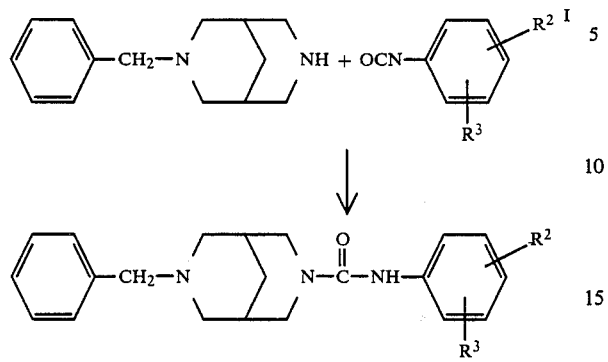

This is one of several possibilities for the preparation of compounds of the general formula I having a urea group (cf. Houben-Weyl, Meth. d. org. Ch., 4th Edition, E4, page 334 et seq). In the compound I thus obtained, the benzyl radical can be substituted by the radicals R and $R^1$, exactly as described above under A. Equation C:

N,N'-dibenzylbispidone is partially debenzylated (cf. Example 28), benzoylated as above in A and thus converted into a compound of the general formula I. Here, the benzyl radical may be exchanged for another radical

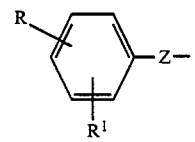

and the carbonyl group can be reduced, for example, with sodium boronate or with a Grignard compound, and the resulting hydroxyl group can be esterified or etherified by a conventional method.

If, in the various possible syntheses, $R^2$ is a primary or secondary amino group, it may be protected, for example, by acetylation, and the acetyl group can be eliminated again hydrolytically after the molecule has been subjected to further reactions.

The bispidine derivatives thus obtained are, if desired, converted into the addition salt with a physiologically tolerated acid. A list of conventional physiologically

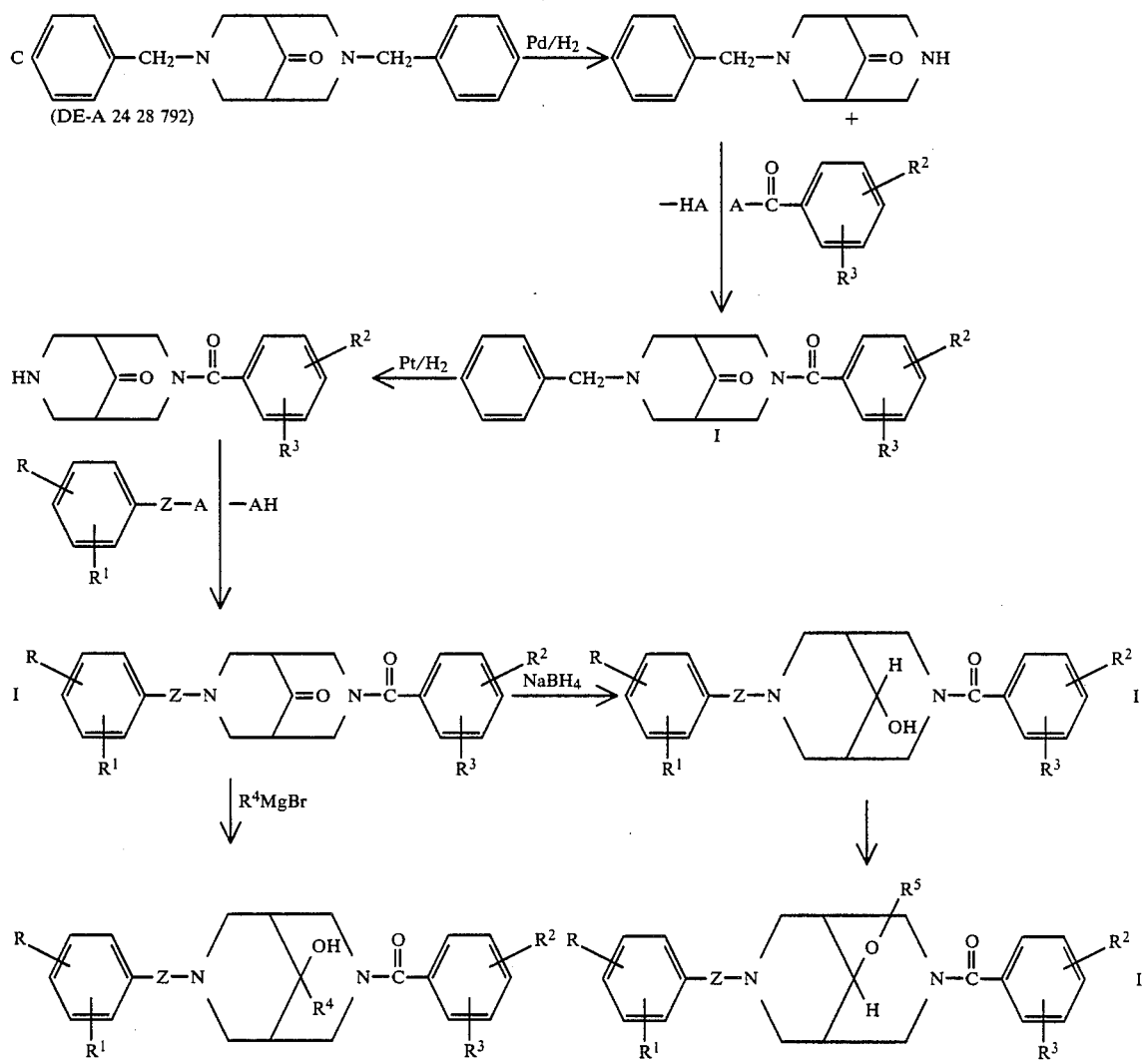

tolerated acids is given in Fortschritte der Arzneimittelforschung, 1966, Birkhäuser Verlag, Vol. 10, pages 224-285, Germany, Switzerland.

The addition salts with acids are, as a rule, obtained in a conventional manner by mixing the free base or a solution thereof with the corresponding acid or a solution thereof in an organic solvent, for example a lower alcohol, such as methanol, ethanol or propanol, a lower ketone, such as acetone, methyl ethyl ketone or methyl isobutyl ketone, or an ether, such as diethyl ether, tetrahydrofuran or dioxane. To improve deposition of crystals, mixtures of the stated solvents can be used. Moreover, pharmaceutically tolerated aqueous solutions of acid addition compounds of bispidine derivatives of the formula I can be prepared by dissolving the free base in an aqueous acid solution.

The present invention furthermore relates to therapeutic agents for topical and especially systemic use, which contain a compound of the formula (I) as the active compound, in addition to conventional carriers or diluents, and to the use of a compound of the formula (I) for the preparation of a drug, in particular an antiarrhythmic agent.

The novel compounds have a good antiarrhythmic Class III action, as the following experiment shows:

The experimental animals used are male and female Pirbright white guinea pigs weighing from 300 to 500 g. Anesthesia is effected with 1.5 g/kg of urethane administered intraperitoneally. The substances are administered intravenously. To measure the ECG conduction times and the heart rate, the II. limb lead is recorded. The relevant parameters are the QT and PQ intervals and the heart rate. From 4 to 6 animals are used per dose. The criterion for Class III action is an increase in the QT interval compared with the values prior to administration of the substance. An increase in the PQ interval and a sharp decrease in the heart rate serve as exclusion criteria. The ED 20% is calculated from the linear relationship between log dose (mg/kg) of the substance and the relative prolongation of the QT interval ($\Delta\%$).

TABLE 1

Antiarrhythmic Class III action in guinea pigs after intravenous administration

| Example No. | Prolongation of the QT interval ED 20% [mg/kg] Mean value |
|---|---|
| 2 | 4.6 |
| 21 | 2.6 |
| 23 | 2.4 |
| 26 | 3.6 |
| Ambasilide | 6.3 |
| D-sotalol | 3.6 |

The novel substances (Table 1) are more effective with regard to QT prolongation than the antiarrhythmic agent ambasilide and some of them are also superior to the known Class III antiarrhythmic agent D-sotalol (Clin. Sci. 69 (1985), 631-636; J. Cardiovascul. Pharmacol. 6 (1984), 1132-1141).

The novel substances are therefore suitable for the treatment of arrhythmias which are otherwise resistant to therapy; in particular, they eliminate ventricular tachycardias which occur after myocardial infarction and are based on a re-entry mechanism (Lit. Cardiac Arrhythmia Ed. P. Brugada, H. J. J. Wellens, Futura Publishing Co., Mount Kisko, New York 1987).

The therapeutic agents or formulations are prepared using the conventional liquid or solid carriers or diluents and the pharmaceutical auxiliaries conventionally used, in accordance with the desired route of administration and with a dose suitable for administration, in a conventional manner, for example by mixing the active compound with the solid or liquid carriers and auxiliaries conventionally used in such preparations.

The agents can be administered perorally, parenterally or topically. Formulations of this type are, for example, tablets, film tablets, coated tablets, capsules, pills, powders, solutions or suspensions, infusion or injection solutions and pastes, ointments, gels, creams, lotions, dusts, solutions or emulsions and sprays.

The therapeutic agents may contain the compounds to be used according to the invention in a concentration of from 0.0001 to 1%, preferably 0.001 to 0.1% for topical administration and preferably in a single dose of from 0.1 to 20 mg per kg body weight for systemic administration, in particular from 0.1 to 4 mg per kg body weight for parenteral administration and from 1 to 20 mg per kg body weight for oral administration, and are administered daily in one or more doses, depending on the nature and severity of the disorders.

Examples of conventionally used pharmaceutical auxiliaries for topical administration are alcohols, such as ethanol, isopropanol, oxyethylated castor oil or oxyethylated hydrogenated castor oil, polyacrylic acid, glycerol monostearate, liquid paraffin, vaseline, wool fat, polyethylene glycol, polypropylene glycol, stearate and oxyethylated fatty alcohol, and those for systemic use are lactose, propylene glycol, ethanol, starch, talc and polyvinylpyrrolidone. If necessary, an antioxidant, for example tocopherol and butylated hydroxyanisole or butylated hydroxytoluene, or flavor improvers, stabilizers, emulsifiers, bleaches, etc. may be added to the preparations. All substances used in the preparation of pharmaceutical formulations must be toxicologically acceptable and compatible with the active compounds used.

EXAMPLE 1

3-(4-acetaminobenzoyl)-7-benzyl-3,7-diazabicyclo[3.3.1]nonane 80.2 g (0.24 mole) of 3-(4-aminobenzoyl)-7-benzyl-3,7-diazabicyclo[3.3.1]nonane (cf. European Pat. No. 62,199) were dissolved in 500 ml anhydrous tetrahydrofuran and cooled with ice. 23.5 g (0.3 mole) of acetyl chloride, dissolved in 50 ml of tetrahydrofuran, were added dropwise, followed by 48.6 g (0.48 mole) of triethylamine at room temperature. The entire mixture was stirred overnight and then evaporated down under reduced pressure. The residue was taken up in water and the solution was extracted 3 times with methylene chloride. The combined organic phases were washed with water, dried and evaporated down under reduced pressure. Yield: 78.1 g, mp.: 208° C.

EXAMPLE 2

7-benzyl-3-(4-chlorobenzoyl)-3,7-diazabicyclo[3.3.1]nonyl hydrochloride 5 g (23 millimoles) of the monobenzylbispidine were dissolved in 100 ml of methylene chloride, and 20 ml of 2M NaOH were added. 4.9 g (28 millimoles) of 4-chlorobenzoyl chloride, dissolved in 10 ml of methylene chloride, were added dropwise while cooling with ice and stirring vigorously. Stirring was continued for 1 hour, the mixture was diluted with water and the methylene chloride phase was isolated and then washed with water and dried, and HCl in ether was added. The oil obtained crystallized from ethyl acetate/ether. Yield: 4.9 g, mp.: 166° C. (×2HCl).

The following compounds were prepared similarly to Example 2:
3. 7-Benzyl-3-(2-methoxybenzoyl)-3,7-diazabicyclo[3.3.1]nonyl hydrochloride, mp.: 162° C. (×HCl).
4. 7-Benzyl-3-(2-chlorobenzoyl)-3,7-diazabicyclo[3.3.1]nonane, mp.: 266° C. (×2HCl).
5. 7-Benzyl-3-(4-dimethylaminobenzoyl)-3,7-diazabicyclo[3.3.1]nonane, mp.: 66° C. (×2HCl).
6. 7-Benzyl-3-(4-methoxybenzoyl)-3,7-diazabicyclo[3.3.1]nonane, mp.: 119° C. (×HCl).
7. 7-Benzyl-3-(4-cyanobenzoyl)-3,7-diazabicyclo[3.3.1]nonane, mp.: 170° C. (×2HCl).
8. 7-Benzyl-3-(2-methylbenzoyl)-3,7-diazabicyclo[3.3.1]nonane, mp.: 243° C. (×HCl).
9. 7-Benzyl-3-(4-bromobenzoyl)-3,7-diazabicyclo[3.3.1]nonane, mp.: 166° C. (×2HCl).
10. 7-Benzyl-3-(4-methylbenzoyl)-3,7-diazabicyclo[3.3.1]nonane, mp.: 133° C. (×2HCl).
11. 7-Benzyl-3-(4-fluorobenzoyl)-3,7-diazabicyclo[3.3.1]nonane, mp.: 133° C. (×2HCl).
12. 7-Benzyl-3-(4-trifluoromethylbenzoyl)-3,7-diazabicyclo[3.3.1]nonane, mp.: 89° C.

EXAMPLE 13

3-(3-aminobenzoyl)-7-benzyl-3,7-diazabicyclo[3.3.1]nonane 10 g (46 millimoles) of monobenzylbispidine were dissolved in 100 ml of methylene chloride, and 20 ml of 2M Sodium hydroxide solution were added. 9 g (48.5 millimoles) of 3-nitrobenzoyl chloride, dissolved in 30 ml of methylene chloride, were added dropwise while cooling with ice and stirring. Stirring was continued for 1 hour and the organic phase was separated off and then washed with water, dried and evaporated down under reduced pressure. 11.5 g of 7-benzyl-3-(3-nitrobenzoyl)-3,7-diazabicyclo[3.3.1]nonane were obtained.

10.5 g (28.8 millimoles) of this nitro derivative were dissolved in 250 ml of methanol, 0.5 g of 5% strength platinum/carbon was added and hydrogenation was carried out until all the hydrogen had been absorbed. Thereafter, the catalyst was filtered off and the filtrate was filtered under reduced pressure. The residue was dissolved in methylene chloride, the solution was washed with 2M sodium hydroxide solution and water and dried, and HCl in ether was added. The oil isolated crystallized from acetone. Yield: 9.75 g, mp.: 235° C. (×2HCl).

The following were prepared similarly to Example 13:
14. 3-(4-amino-2-chlorobenzoyl)-7-benzyl-3,7-diazabicyclo[3.3.1]nonane, mp.: 213° C. (×2HCl).
15. 3-(2-aminobenzoyl)-7-benzyl-3,7-diazabicyclo[3.3.1]nonane, mp.: 178° C.

EXAMPLE 16

3-(4-aminobenzoyl)-7-(4-chlorobenzyl)-3,7-diazabicyclo[3.3.1]nonane 78.0 g (0.21 mole) of 3-(4-acetaminobenzoyl)-7-benzyl-3,7-diazabicyclo[3.3.1]nonane (cf. Example 1) were dissolved in 1.3 l of methanol, and 3.0 g of 10% strength palladium/carbon were added. Hydrogenation was carried out until an equimolar amount of hydrogen had been consumed. The reaction mixture was filtered and the filtrate was evaporated down under reduced pressure. Crystalline 3-(4-acetaminobenzoyl)-3,7-diazabicyclo[3.3.1]nonane was obtained. Yield: 59 g, mp.: 186°–189° C.

5.0 g (17.4 millimoles) of this product were dissolved together with 3.6 g (17.5 millimoles) of 4-chlorobenzyl bromide and 5 ml of triethylamine in 100 ml of methanol and stirred for 60 hours at 25° C. Thereafter, the solution was evaporated down under reduced pressure and the residue was dissolved in methylene chloride. The organic phase was washed with 2M sodium hydroxide solution and water, dried and evaporated down under reduced pressure. 6.6 g of 3-(4-acetaminobenzoyl)-7-(4-chlorobenzyl)-3,7-diazabicyclo[3.3.1]nonane of melting point 181° C. were obtained.

6.6 g (16 millimoles) of the above product were dissolved in 50 ml of methanol, and 60 ml of 0.1M sodium hydroxide solution were added. The mixture was heated at 100° C. for 3 hours. The resulting precipitate was isolated and recrystallized from toluene/ethanol. Yield: 2.3 g, mp.: 255° C.

The following compounds were prepared from 3-(4-acetaminobenzoyl)-3,7-diazabicyclo[3.3.1]nonane similarly to Example 16:
17. 3-(4-aminobenzoyl)-7-(3-cinnamyl)-3,7-diazabicyclo[3.3.1]nonane, mp.: 194° C. (×2HCl).
18. 3-(4-aminobenzoyl)-7-(2-phenylethyl)-3,7-diazabicyclo[3.3.1]nonane, mp.: 167° C.
19. 3-(4-aminobenzoyl)-7-(2,6-dichlorobenzyl)-3,7-diazabicyclo[3.3.1]nonane, mp.: 213° C.

EXAMPLE 20

7-Benzyl-3-(methanesulfonylamido)-3,7-diazabicyclo[3.3.1]nonane 1.9 g (16.4 millimoles) of methanesulfonyl chloride were added dropwise at 5°–10° C. to 5.0 g (14.9 millimoles) of 3-(4-aminobenzoyl)-7-benzyl-3,7-diazabicyclo[3.3.1]nonane, which was dissolved in 50 ml of pyridine. Stirring was continued for 16 hours at the stated temperature. The reaction mixture was poured onto 200 ml of water, and the precipitated product was freed from water by decantation. The product obtained was recrystallized from ethyl acetate. Yield: 4.1 g, mp.: 172° C.

EXAMPLE 21

7-Benzyl-3-(4-methylphenylcarbamyl)-3,7-diazabicyclo[3.3.1]nonane 2.6 g (0.012 mole) of monobenzylbispidine 1.6 g (0.012 mole) of 4-methylphenyl isocyanate and 0.25 ml of triethylamine were dissolved in 25 ml of naphtha, and the solution was refluxed for 1 hour. The resulting precipitate was isolated and recrystallized from naphtha/2-propanol. Yield: 2.5 g, mp.: 150° C.

The following compounds were prepared from monobenzylbispidine, similarly to Example 21:
22. 7-Benzyl-3-(4-methoxyphenylcarbamyl)-3,7-diazabicyclo[3.3.1]nonane, mp.: 161° C.
23. 7-Benzyl-3-(4-chlorophenylcarbamyl)-3,7-diazabicyclo[3.3.1]nonane, mp.: 175° C.
24. 7-Benzyl-3-(phenylcarbamyl)-3,7-diazabicyclo[3.3.1]nonane, oil.

EXAMPLE 25

3-(4-aminophenylcarbamyl)-7-benzyl-3,7-diazabicyclo[3.3.1]nonane 5.2 g (24 millimoles) of monobenzylbispidine, 3.95 g (24 millimoles) of 4-nitrophenyl isocyanate and 0.50 ml of triethylamine were combined in 50 ml of naphtha and then refluxed for 1 hour. The resulting precipitate was isolated and recrystallized from methanol/isopropanol. Yield: 6.7 g.

5.6 g (14.7 millimoles) of the resulting nitro compound were taken up in 100 ml of methanol, 0.6 g of 5% strength platinum/carbon was added and hydrogenation was carried out at room temperature and under 1 bar. The mixture was then filtered and the filtrate was evaporated down under reduced pressure. Yield: 4.5 g, mp.: 77° C.

EXAMPLE 26

3-(Phenylcarbamyl)-7-(4-chlorobenzyl)-3,7-diazabicyclo[3.3.1]nonane 18.7 g (55.7 millimoles) of 7-benzyl-3-(phenylcarbamyl)-3,7-diazabicyclo[3.3.1]nonane were dissolved in 170 ml of methanol and 30 ml of glacial acetic acid. 1.1 g of 10% strength palladium/carbon were added and hydrogenation was carried out at room temperature until an equimolar amount of hydrogen had been consumed. Thereafter, the mixture was filtered and the filtrate was rendered alkaline with sodium hydroxide solution and evaporated down under reduced pressure. The residue was extracted 3 times with methylene chloride. The resulting organic phase was dried, and evaporated down under reduced pressure. Recrystallization was effected from ethyl acetate. Yield: 8.7 g.

3.5 g (14.3 millimoles) of the resulting amine, 3.2 g (20.0 millimoles) of 4-chlorobenzyl chloride and 5 ml of triethylamine were dissolved in 50 ml of methanol and the solution was sttirred for 60 hours at room temperature and then heated for 2 hours at 60° C. The reaction mixture was then rendered weakly alkaline with sodium hydroxide solution and evaporated down under reduced pressure. The residue was extracted 3 times with methylene chloride and the organic phase was dried and evaporated down under reduced pressure. Recrystallization was effected from ethyl acetate. Yield: 2.0 g, mp.: 161° C.

The following was prepared similarly to Example 26:
27. 7-(4-Nitrobenzyl)-3-(phenylcarbamyl)-3,7-diazabicyclo[3.3.1]nonane, mp.: 187° C. (×HCl)

EXAMPLE 28

7-Benzyl-3-(4-chlorobenzoyl)-3,7-diazabicyclo[3.3.1]-non-9-one 32.0 g (0.1 mole) of 3,7-dibenzyl-3,7-diazabicyclo[3.3.1]non-9-one were dissolved in 250 ml of methanol, 1 g of 10% strength palladium/carbon was added and hydrogenation was carried out until an equimolar amount of hydrogen had been consumed. The mixture was then filtered and the filtrate was evaporated down under reduced pressure. 14.1 g of 3-benzyl-3,7-diazabicyclo[3.3.1]non-9-one of melting point 110° C. were obtained.

14.0 g (60.9 millimoles) of the resulting product were dissolved in 100 ml of methylene chloride, 100 ml of 2M sodium hydroxide solution were added and the mixture was cooled with ice. 16.0 g (91.3 millimoles) of 4-chlorobenzoyl chloride, dissolved in methylene chloride, were added dropwise and stirring was continued for a further 3 minutes. The organic phase was separated off, washed with sodium hydroxide solution and water, dried and evaporated down under reduced pressure. Yield: 22 g, mp.: 154° C. (×HCl).

EXAMPLE 29

7-Benzyl-3-(4-chlorobenzoyl)-3,7-diazabicyclo[3.3.1]-non-9-ol 14.2 g (38.5 millimoles) of the ketone obtained according to Example 28 were dissolved in 150 ml of methanol, and 1.5 g (39.5 millimoles) of sodium borohydride were added a little at a time. Stirring was carried out for 1 hour at room temperature, after which 70 ml of 1M hydrochloric acid were added dropwise. The solution was evaporated down under reduced pressure, the residue was dissolved in methylene chloride and the solution was washed with sodium hydroxide solution and water, dried and evaporatted down. Yield: 14 g, mp.: 167° C.

EXAMPLE 30

7-Benzyl-3-(4-chlorobenzoyl)-3,7-diazabicyclo[3.3.1]-non-9-yl benzoate 3.0 g (8.1 millimoles) of the above alcohol were dissolved in 50 ml of pyridine, and a solution of 2.3 g (16.2 millimoles) of benzoyl chloride in 30 ml of pyridine was added dropwise at 5°-10° C. The mixture was stirred overnight. Thereafter, the reaction mixture was diluted with 500 ml of water and extracted twice with $CH_2Cl_2$. The organic phase was washed with water, dried and evaporated down and the residue was recrystallized from ethyl acetate. Yield: 2.0 g, mp.: 165° C.

EXAMPLE 31

7-Benzyl-3-(4-nitrobenzoyl)-3,7-diazabicyclo[3.3.1]non-9-one 11.3 g (49.1 millimoles) of 7-benzyl-3,7-diazabicyclo[3.3.1]non-9-one were dissolved in 100 ml of methylene chloride and 100 ml of 2M sodium hydroxide solution were added. A solution of 13.7 g (73.7 millimoles) of 4-nitrobenzoyl chloride in 30 ml of methylene chloride was added dropwise at 0° C., and stirring was continued for 1 hour. The organic phase was separated off, washed with sodium hydroxide solution and water, dried and evaporatted down. The residue was recrystallized from acetone. 10.5 g of a product of melting point 138° C. were obtained.

EXAMPLE 32

7-Benzyl-3-(4-nitrobenzoyl)-3,7-diazabicyclo[3.3.1]non-9-ol 15.0 g (39.6 millimoles) of the ketone obtained according to Example 31 were dissolved in 150 ml of methanol. 1.5 g (39.6 millimoles) of sodium borohydride were added a little at a time at room temperature, and stirring was continued for 1 hour. Thereafter, 50 ml of 2M hydrochloric acid were added dropwise, and the mixture was stirred for 2 hours at room temperature and evaporated down under reduced pressure. The residue was partitioned between methylene chloride and sodium hydroxide solution, and the organic phase was separated off, washed again with sodium hydroxide solution and then with water, dried and then evaporated down. Crystallization was effected from ethyl acetate, and 11.5 g of a product of melting point 210° C. were obtained.

EXAMPLE 33

7-Benzyl-3-(4-nitrobenzoyl)-3,7-diazabicyclo[3.3.1]non-9-yl benzoate 4.0 g (10.5 millimoles) of the alcohol obtained according to Example 32 were dissolved in 50 ml of pyridine. 3.0 g (21 millimoles) of benzoyl chloride were added dropwise at 5°–10° C. and sttirring was continued for 3 hours at room temperature. The reaction mixture was then diluted with 500 ml of water and extracted twice with ether. The organic phase was washed twice with water, dried and evaporated down. The residue obtained was recrystallized from ethyl acetate to give 3.8 g of a product of melting point 180° C.

EXAMPLE 34

3-(4-aminobenzoyl)-7-benzyl-3,7-diazabicyclo[3.3.1]-non-9-yl benzoate 3.8 g (7.8 millimoles) of the ester obtained according to Example 33 were dissolved in 250 ml of methanol, and hydrogenation was carried out using 0.1 g of 5% strength platinum/carbon at room temperature. Thereafter, the mixture was filtered and the filtrate was evaporated down under reduced pressure. 1.1 g of a product of melting point 99° C. were obtained by recrystallization of the residue from ethyl acetate.

The following were prepared by catalytic hydrogenation, similarly to Example 34:

35.         3-(3-aminobenzoyl)-7-benzyl-3,7-diazabicyclo[3.3.1]non-9-one, mp.: 235° C. (×HCl).

36.         3-(4-aminobenzoyl)-7-benzyl-3,7-diazabicyclo[3.3.1]non-9-ol, mp.: 232° C. (×2HCl).

EXAMPLE 37

7-Benzyl-3-(4-chlorobenzoyl)-9-ethyl-3,7-diazabicyclo[3.3.1]non-9-ol

A solution of 5.0 g (13.6 millimoles) of 7-benzyl-(4-chlorobenzoyl)-3,7-diazabicyclo[3.3.1]non-9-one (Example 28) and 50 ml of anhydrous tetrahydrofuran was added dropwise at room temperature to the Grignard compound of 0.7 g (27.2 millimoles) of magnesium and 3.4 g of ethyl bromide in ether. Stirring was carried out for 1 hour, followed by hydrolysis with 50 ml of watter and a little 2M hydrochloric acid. The mixture was evaporated down under reduced pressure. The residue was partitioned between methylene chloride and 2M sodium hydroxide solution, and the organic phase was separated off, washed again with 2M sodium hydroxide solution and water, dried and evaporated down. Yield: 3.4 g, mp.: 72° C.

We claim:

1. A bispidine derivative of the formula (I):

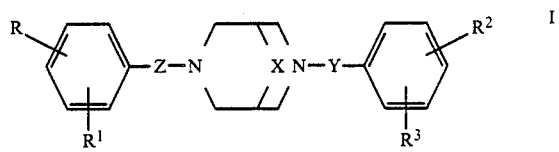

wherein R, $R^1$ and $R^3$ are identical or different and are each hydrogen, $C_1$-$C_4$-alkyl, halogen or $C_1$-$C_4$-alkoxy; X is —$CH_2$—, —C(O)— or —C($R^6$)($OR^7$)—, wherein $R^6$ is hydrogen or $C_1$-$C_4$-alkyl and $R^7$ is hydrogen, $C_1$-$C_4$-alkyl or a moiety of the formula:

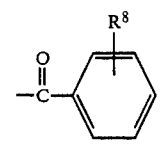

wherein $R^8$ is hydrogen, $C_1$-$C_4$-alkyl, halogen or $C_1$-$C_4$-alkoxy; Y is —CONH—; Z is $C_1$-$C_4$-alkylene and $R^2$ is —$NO_2$, —$NH_2$, $C_1$-$C_4$-alkyl, halogen, —CN, $C_1$-$C_4$-alkoxy, —$NHSO_2CH_3$, —$CF_3$, —NH-acetyl or —$NR^9R^{10}$, wherein $R^9$ is $C_1$-$C_4$-alkyl and $R^{10}$ is hydrogen or $C_1$-$C_4$-alkyl; or the pharmaceutically-acceptable salts thereof.

2. A pharmaceutical composition which comprises, as the active compound, an effective amount of a bispidine derivative as claimed in claim 1, in conjunction with a pharmaceutically-acceptable carrier.

3. A pharmaceutical composition suitable for topical administration, which comprises from 0.0001 to 1% by weight of a bispidine derivative as claimed in claim 1, in conjunction with a pharmaceutically-acceptable carrier.

4. A pharmaceutical composition suitable for parenteral administration, which comprises, per single dose, from 5 to 200 mg of a bispidine derivative as claimed in claim 1, in addition to pharmaceutically-acceptable carrier.

5. The pharmaceutical composition as claimed in claim 3, which comprises from 0.001 to 0.1% by weight of said bispidine derivative.

6. The bispidine derivative as claimed in claim 1, wherein $R^3$ is hydrogen.

7. The bispidine derivative as claimed in claim 1, wherein X is —$CH_2$— or —C(O)—.

8. The bispidine derivative as claimed in claim 1, wherein Z is methylene.

9. The pharmaceutical composition as claimed in claim 2, wherein $R^3$ is hydrogen.

10. The pharmaceutical composition as claimed in claim 2, wherein X is —$CH_2$— or —C(O)—.

11. The pharmaceutical composition as claimed in claim 2, wherein Z is methylene.

* * * * *